(12) United States Patent
Pusterla et al.

(10) Patent No.: US 7,260,484 B2
(45) Date of Patent: Aug. 21, 2007

(54) METHOD FOR CARRYING OUT ION MOBILITY SPECTROMETRY ANALYSES

(75) Inventors: Luca Pusterla, Milan (IT); Antonio Bonucci, Milan (IT); Roberto Giannantonio, Oleggio (IT); Marco Succi, Milan (IT)

(73) Assignee: Saes Getters S.p.A., Lainate MI (IT)

( * ) Notice: Subject to any disclaimer, the term of this patent is extended or adjusted under 35 U.S.C. 154(b) by 97 days.

(21) Appl. No.: 11/040,076

(22) Filed: Jan. 21, 2005

(65) Prior Publication Data

US 2005/0178957 A1   Aug. 18, 2005

Related U.S. Application Data

(63) Continuation of application No. PCT/IT03/00429, filed on Jul. 10, 2003.

(30) Foreign Application Priority Data

Jul. 22, 2002 (IT) ............. MI2002A1616
Jul. 29, 2002 (IT) ............. MI2002A1686

(51) Int. Cl.
G01N 27/64 (2006.01)
(52) U.S. Cl. ............. 702/24; 702/22; 702/27; 702/30; 436/103; 436/109; 250/288; 250/286; 250/282
(58) Field of Classification Search ........... 702/24, 702/22, 27, 30; 436/103, 109; 250/288, 250/286, 282
See application file for complete search history.

(56) References Cited

U.S. PATENT DOCUMENTS

| | | |
|---|---|---|
| 5,200,614 A | 4/1993 | Jenkins |
| 5,405,781 A | 4/1995 | Davies et al. |
| 5,457,316 A | 10/1995 | Cohen et al. |
| 5,510,268 A | 4/1996 | Döring et al. |
| 5,723,861 A | 3/1998 | Carnahan et al. |
| 5,955,886 A | 9/1999 | Cohen et al. |
| 6,011,258 A | 1/2000 | Baumbach et al. |
| 6,229,143 B1 | 5/2001 | Wernlund |
| 6,291,821 B1 | 9/2001 | Danylewych-May et al. |

FOREIGN PATENT DOCUMENTS

| | | |
|---|---|---|
| WO | WO 02/052255 A1 | 7/2002 |
| WO | WO 02/099405 A2 | 12/2002 |

*Primary Examiner*—John Barlow
*Assistant Examiner*—Hien Vo
(74) *Attorney, Agent, or Firm*—Akin Gump Strauss Hauer & Feld L.L.P.

(57) ABSTRACT

A method for carrying out analyses of a gas comprising one or more species $S_i$, $S_j$, . . . , $S_n$ by using of ion mobility spectrometry includes in carrying out two subsequent analyses in different conditions and comparing the results of these two analyses. The different conditions in the two analyses are such as to modify either the residence time of the ions corresponding to the species in the reaction zone or in the drift zone of the ion mobility spectrometer, or, selectively, the concentration of at least one of these ions.

10 Claims, 1 Drawing Sheet

US 7,260,484 B2

METHOD FOR CARRYING OUT ION MOBILITY SPECTROMETRY ANALYSES

CROSS-REFERENCE TO RELATED APPLICATIONS

This application is a continuation of International Application No. PCT/IT2003/00429, filed Jul. 10, 2003, which was published in the English language on Jan. 29, 2004, under International Publication No. WO 2004/010131 A1 and the disclosure of which is incorporated herein by reference.

BACKGROUND OF THE INVENTION

The present invention relates to differential methods for carrying out ion mobility spectrometry analyses, and in particular to the simultaneous analysis of more impurities contained in a very pure gas, such as those employed in the microelectronic industry.

Ion mobility spectrometry is generally known in the field of chemical analyses with the abbreviation IMS, which also indicates the instrument for carrying out the analytic technique (in this case abbreviating the terms Ion Mobility Spectrometer).

The interest for the IMS technique comes from its extremely high sensitivity, associated with the reduced size and cost of the instrument. By operating in suitable conditions it is possible to detect species in gas or vapor phase in a gas mixture in picograms quantities (pg), i.e., $10^{-12}$ grams), or in part per trillion concentrations (ppt), i.e., equal to a molecule of analyzed substance per $10^{12}$ molecules of sample gas. The gas forming most of the gas mixture will be referred to hereinafter as "carrier gas," while the mixture itself will be referred to hereinafter as "sample gas."

There are many application fields of this technique, both in civilian sectors (in particular, for the detection in the industry of inorganic or organic contaminants in clean rooms or of noxious species in the industrial exhausts) and in military sectors (in particular, for the detection of the presence of explosive or toxic substances, such as nerve gases). IMS analysis methods and instruments are disclosed, for example, in U.S. Pat. Nos. 5,457,316, (Cohen et al.); 5,955,886 (Cohen et al.); and 6,229,143 (Werlund).

The general geometrical structure of an IMS instrument is shown in the only attached drawing. The instrument is essentially made up of a cylindrical chamber C having at one end the inlet IC for the sample gas, around which an inlet electrode ER and a ionizing member IM are arranged, and at the opposite end a detector D for charged particles. Detector D is normally kept at the ground potential, while the inlet electrode ER is kept at a potential higher than that of the detector (instrument working in the positive mode) or lower (negative mode) than said detector potential. For simplicity and clarity, in the remainder of the description, reference will always be made to the use of an IMS instrument in the positive mode (the ions corresponding to the analyzed species will be indicated as positive ions), which corresponds to the most common condition of use, but all these considerations are also valid for the use in the negative mode. An electrifiable grid G divides chamber C into two zones, referred to in the field as the "reaction zone" (i.e., on the inlet side of the instrument) indicated in the following with RZ and the "drift zone" (i.e. on the detector side of the instrument) indicated in the flowing with DZ. Grid G generally comprises two alternated series of linear and parallel conductive members, commonly metal wires, which are arranged perpendicularly to the longitudinal axis x of chamber C. A series of electrodes $E_i$(i=1, ..., n), generally annular, each set at a suitable voltage for creating between the inlet electrode ER and detector D an electric field suitable for transporting the ions toward said detector, is arranged along the walls of the two zones RZ and DZ. A screen grid SG is arranged between the last electrode $E_n$ and detector D to avoid the creation on the latter of an "image charge," (i.e., the build up of an electrostatically induced charge on detector D. The wires of grid G are inserted into the central cavity of an electrode $E_g$, referred to hereinafter as grid electrode, from which are however electrically insulated. During their motion, the ions are slowed down by a gas usually counter-flowing with respect to the ion motion direction. This gas is introduced from a duct DC at the end of chamber C where detector D is located and is expelled by an outlet OC at the opposite end. The counter-flowing gas, defined as "drift gas" in the field, is an ultra-pure gas which can be the same as the carrier gas or different.

The ionizing member IM is commonly a beta radiation source comprising $^{63}$Ni. According to the working mode, the ions with a charge opposite to the charge of the inlet electrode ER are neutralized on or near the inlet electrode ER, while the ions with a charge of the same sign as this electrode undergo a repulsion and are accelerated in the reaction zone. The first ionization produces essentially exclusively ions of the carrier gas, due to its concentration being higher by several orders of magnitude than that of the other species, generally present as traces. The primary ions corresponding to the carrier gas are called "reactant ions" in the field. In the reaction zone, the charge of the reactant ions is distributed among the present species according to their electron or proton affinities, to their ionization potentials or to their electronegativity, according to reactions of the kind:

$$R^+ + S_i \rightarrow R + S_i^+ \qquad (I)$$

wherein $R^+$ represents a reactant ion, R a neutral molecule deriving from the neutralization of the reactant ion (that is, a carrier gas molecule), $S_i$(i=1, ..., n) a molecule of the i-th species to be analyzed and $S_i^+$ the ion corresponding to $S_i$. The ions $S_i^+$ often give rise to complex species due to the association with one or more neutral molecules, but for ease of notation and without losing generality, reference will always be made to simple ions hereinafter.

All these ions are transported by the electric field toward the electrifiable grid G. The grid members are grouped in two mutually alternated series, so that each member of one series has two members of the other series as the closest members. The two series of grid members are normally biased with potential values higher and lower, respectively, than the potential of the grid electrode $E_g$. A transversal electric field generally stronger than the one along the longitudinal axis of the chamber at that point is thus created on the grid plane, so that the ions present in the reaction zone are accelerated toward the members of one of the two series constituting the grid and neutralized. In these conditions, the grid is "closed" and prevents the ions from passing toward the drift zone. When the analysis is to be carried out, the two series of grid members are brought at the same potential of the grid electrode, thereby canceling the transversal field. In these conditions, the grid is "open" so that the ions can advance into the drift zone. The grid opening lasts generally from some tens to some hundreds of microseconds (ms) and during this time a portion of the ions present in the reaction zone is transferred to the drift zone. In particular, the grid is crossed by the ions contained in a cylindrical volume in the reaction zone adjacent to the grid, the height of which is determined by the relation:

$$l_a = v_i \times t_a \quad \text{(II)}$$

where $l_a$ is the height of the cylindrical volume, $v_i$ is the motion speed of the ion $S_i^+$ and $t_a$ is the opening time of the grid. The initial or central instant of the grid opening time slot is commonly assumed as the "time zero," i.e., the analysis start.

In the drift zone DZ, the ions are transported toward detector D with a motion speed which is the resultant of the acceleration due to the presence of the axial electric field and the deceleration due to the collisions with the drift gas. In particular, the motion speed of the i-th ion depends linearly on the electric field and is directly proportional to the temperature T and inversely proportional to the pressure P, according to the effect that the latter two terms have on the viscosity of the drift gas. While the acceleration due to the electric field acts to the same extent on the ions having the same charge (but in the IMS all the ions generally have a unitary charge), the deceleration acts in a different way on the ions according to the different size, shape and mass of the same, so that each ion has a characteristic motion speed and therefore a crossing time of the drift zone (defined as "drift time" in the field) generally different from that of the other ions. By recording the charges collected on detector D, a spectrum is obtained comprising ion current peaks as a function of the time elapsed from the test start. The intensity of each peak in the spectrum is proportional to the amount of charge $C_{Si}^+$ transported by the ion $S_i^+$ which caused the peak.

Through calibrating tests, in which sample gases containing a single species $S_i$ are analyzed, it is possible, in principle, to obtain data such as speed and drift time of the ionic species $S_i^+$ in a given gas and at given temperature and pressure conditions, as well as the efficiency of the reaction I for that species. In ideal conditions and operating in the same conditions of the calibrating tests, the data could be employed in an IMS analysis for determining the presence of a species $S_i$ in the gas under exam according to the position of the peaks in the spectrum and its concentration according to the relative size of the different peaks.

However, in the real analyses, the situation is much more complex, due to many phenomena which affect the above theoretical conditions.

A first phenomenon includes the possible presence of unexpected and unknown species $U_i(i=1, \ldots, m)$, for which calibration data are not available and that may interfere with the analysis by subtracting charge from the ions $S_i^+$ or from the ions $R^+$ according to reactions of the kind:

$$S_i^+ + U_i \rightarrow S_i + U_i^+ \quad \text{(III)}$$

The result is a spectrum in which the peaks relating to the ions $S_i^+$ and the peak relating to the ion $R^+$ (defined in the field "reactant ion peak", or with its abbreviation RIP, which will be used hereinafter) have an intensity that is lower than in theoretical conditions or may even disappear, while there are peaks which cannot have an attribution.

Furthermore, the species formed in the reaction zone may react with other neutral species, already in the reaction zone or in the drift zone, with reactions of the kind:

$$S_i^+ + S_j \rightarrow S_i + S_j^+ \quad \text{(IV)}$$

or $$S_i^+ + S_i \rightarrow (S_i)_2^+ \quad \text{(V)}$$

Each reaction (IV), (V) proceeds to different degrees and at different rates according to the different kinetics and equilibrium constants for each reaction. These reactions cause the modification of the concentrations of the ions reaching the detector of the IMS instrument with respect to the concentrations initially formed by the direct reaction with the $R^+$ ions, so that the ions corresponding to a species could completely disappear and the latter cannot be detected anymore in the analysis. Reference can be made to the book "Ion Mobility Spectrometry", edited by G. A. Eiceman and Z. Karpas, published in 1994 by CRC Press, for a presentation of the complex charge transfer principles involved in these reactions.

Furthermore, gases like $O_2$, CO, $H_2$, $H_2O$, etc., coming for instance from previous analyses, can be present on the inner surfaces of the instrument (such as the inner walls of the chamber, electrodes, etc.), either chemisorbed or physically adsorbed. Alternatively, these gases can be dissolved in the materials constituting the instrument. For example, steel, which the chamber is generally made of, normally contains hydrogen. These gases are released both in the reaction zone and in the drift zone. During the analysis, they form additional species $B_i(i=1, \ldots, r)$ which come into reactions of type I, III or IV. When these reactions occur in the reaction zone, a charge is removed from the species initially present in the sample gas and spurious peaks appear in the final spectrum. The same reactions, when they occur in the drift zone, may instead lead to spectrum distortions. Unlike the ions of the species $S_i$, which come into the drift zone all at the same time and start from the same position (the grid), the ions corresponding to these species are formed at different points of the drift zone, and therefore, reach the detector at different times according to the formation point: the consequence is that between the spectrum peaks the baseline is not zero as it should be in theory, but there is instead a non-null spectrum "background" which complicates the determination of the area of the peaks or may make it practically impossible in the case of peaks with a lower intensity. The presence of the species $B_i$ also involves other drawbacks. First, these may react with species $S_i^+$ through reactions of type III or IV in the drift zone, thus causing an undesired attenuation of the charge quantity transferred by the species $S_i^+$ to the detector and a consequent reduction of the instrument sensitivity. Second, the interaction of species $B_i$ with the species $R^+$ in the drift zone may cause an undesired attenuation of the RIP, with a consequent reduction of the upper reading threshold of the instrument.

BRIEF SUMMARY OF THE INVENTION

Briefly stated, the present invention comprises a method for carrying out analyses of a gas including one or more species $S_i(i=1, \ldots, n)$ by using ion mobility spectrometry. The method includes carrying out a first test with a first set of values of the experimental parameters and carrying out a second test with a second set of values of the experimental parameters. The second test includes changing only one parameter chosen among the concentration $[S_i]$ of the species giving rise to ions $S_i^+(i=1, \ldots, n)$, the residence time of the ions in the reaction zone and the residence time of the ions in the drift zone of an ion mobility spectrometer. The method also includes employing the data obtained in the two tests in a relation by expressing the charge transferred by the i-th ion to the detector of the spectrometer $C_{si}^+$ as a function of test parameters, thereby obtaining two equations. The two equations are divided by one another to eliminate from the calculation invariant parameters and to obtain as a result of the division at least one parameter that can then be reintroduced in each of the two equations above, thereby obtaining the concentration [$S_i$] of at least one of the species $S_i$(i=1, ..., n).

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
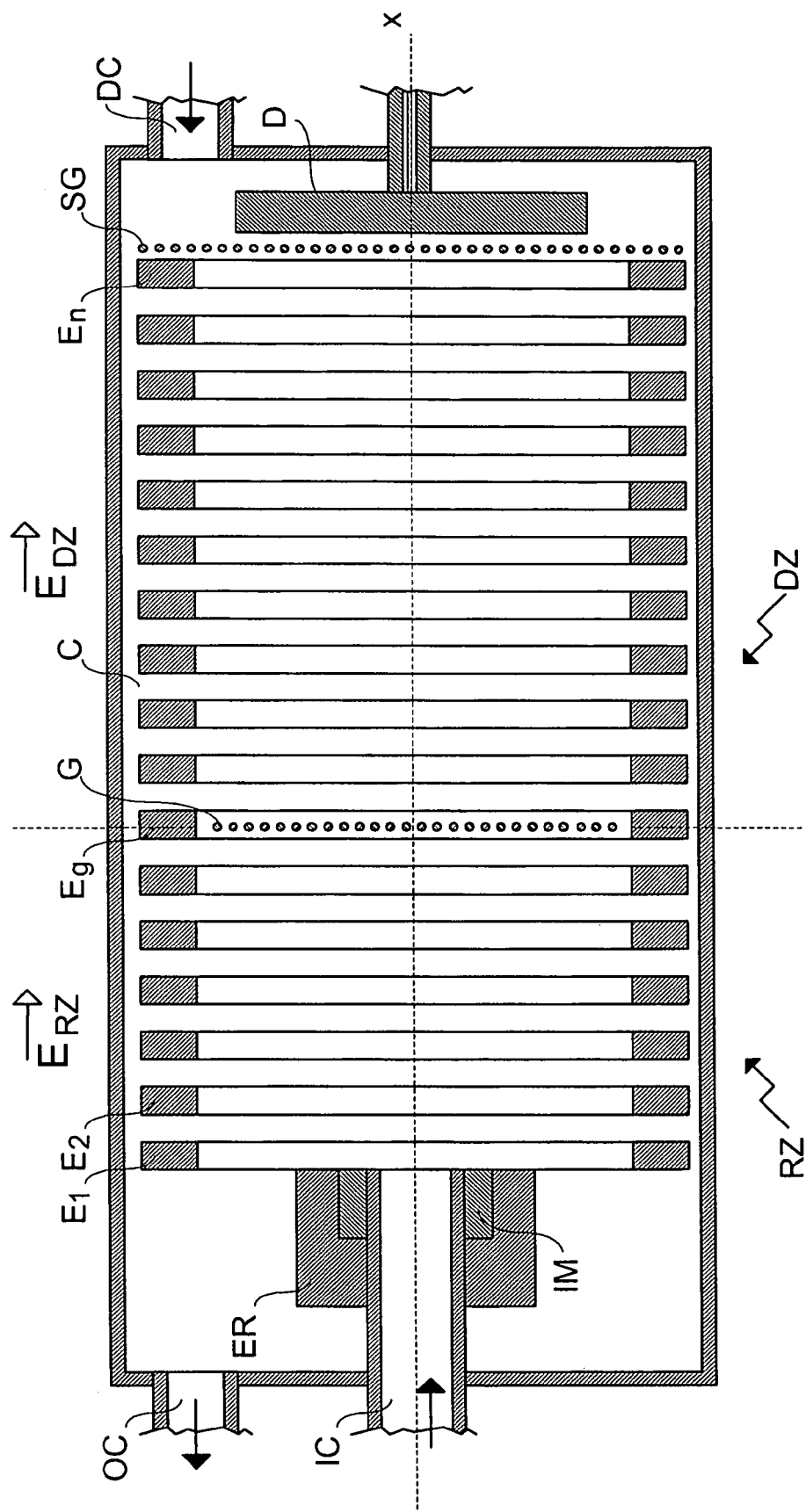
FIG. 1 is a longitudinal cross-section view of the chamber of an IMS instrument usable by preferred embodiment of the present invention.

Further advantages and features of the method according to the present invention will become clear to those skilled in the art from the following detailed and non-limiting description of some embodiments thereof, with reference to the sole FIGURE, which shows a longitudinal cross-section view of the chamber of an IMS instrument.

It is generally acknowledged that an IMS spectrum could in principle be interpreted and fully analyzed, thereby obtaining the concentration of the species present as impurities in the gas under analysis. However, such interpretation is complicated by the need to know several numeric parameters that are very difficult to determine. In particular, to carry out a complete interpretation of an IMS spectrum, all of the kinetic constants $K_{R-Si}$ for reactions of type I are required to be known, as well as the kinetic constants $K_{Si-Sj}$ and $K_{Si-Uj}$ of side reactions of type III and IV. The values of these constants for each species $S_i$ could be obtained through a suitable calibration procedure, but that would require an extremely long and burdensome set of preparatory tests. The problem is generally faced by making assumptions on the phenomena occurring during the analysis, e.g., that the entity of side-reactions of type III, IV and V, or with species $B_i$, can be neglected. This leads to a simplification of the calculations, but is an approximation that introduces errors in the result of the analysis.

The method in accordance with preferred embodiments of the present invention includes carrying out two subsequent analyses with the IMS instrument changing one parameter in the two tests, obtaining a series of data (referred to hereinafter as "primary data") from the two spectra obtained as direct results of the analysis, and employing the primary data of the two analyses in a mathematical relation thus obtaining two equations, each one relating to one of the two subsequent analyses. By comparing these two equations (in particular, dividing one by another), it is possible to eliminate from the calculation the unknown values or parameters that are generally neglected in the prior art method. This permits performing calculations that lead to the final results of the analysis, expressed as the concentration of at least one of the species $S_i$(i=1, ..., n), that are not affected by the approximation problems of the prior art. Of course, in the methods of the present invention, all experimental parameters apart from the one intentionally changed remain unchanged in the two subsequent analyses.

In a first embodiment thereof, the method of the present invention includes carrying out two IMS tests in such experimental conditions as to modify the residence time of the ionic species $S_i^+$ in the reaction zone of the IMS spectrometer.

During their experimental activity, the inventors have determined that the amount of charge $C_{Si}^+$ transported by the ion $S_i^+$ onto detector D can be represented by the following equation:

$$C_{Si}^+ = [S_i] \times t \times \Delta \times K_{R-Si}/\xi \times \gamma^t \qquad (VI)$$

wherein:

[$S_i$] is the concentration of the species $S_i$;

t is the residence time of the ion $S_i^+$ in the reaction zone RZ, which can be calculated from known quantities, such as the flow speed of the sample gas and of the drift gas, the intensity of the electric field in the reaction zone, the intensity of the electric field in the drift zone, the length of the reaction zone, the length of the drift zone; alternatively, t can be derived from measurable quantities, such as the time of flight of the ion $S_i^+$;

Δ is the difference between the charge quantity directly formed by the ionizing member IM, $C_{R,0}$, and the charge transported onto detector D by the ion $R^+$, $C_R$; Δ is equal to the charge transferred by the reactant ion and therefore to the total charge of all the species $S_i^+$(i=1, ..., n), $U_i^+$(i=1, ..., m), and can thus be obtained by the spectrum resulting from the IMS analysis by calculating the area bounded below all the peaks present in the spectrum (comprising the area bounded below the baseline), except the RIP;

$K_{R-Si}$ is the kinetic constant of the charge transfer reaction from the ion $R^+$ to the species $S_i$ (reaction of type I);

ξ is equal to ln ($C_{R,0}/C_R$) and can be obtained from the spectrum resulting from the IMS analysis by knowing the area bounded below all the peaks present in the spectrum (comprising the area bounded below the baseline) and the area of the RIP only; and γ is a function which considers the reaction constants $K_{Si-Sj}$ and $K_{Si-Uj}$ between the species $S_i$ and all the species $S_j^+$(j=1, ..., n; j≠i), $U_j^+$(j=1, ..., m) and between the species $S_i^+$ and all the species $S_j$(j=1, ..., n), $U_j$(j=1, ..., m) (reactions of type III, IV or V); γ also considers the concentrations of all the species $S_j$(j=1, ..., n; j≠i), $U_j$(j=1, ..., m), i.e. of all the species except $S_i$, but including for instance the species $U_i$ and $B_i$; as IMS analyses are very quick, and carrying out a complete set of tests required for performing a differential method of the invention takes times in the order of seconds, the approximation can be made that these concentrations remain constant during an analysis according to the invention; in these conditions, this function assumes a fixed value. The exponent t in the term $\gamma^t$ which appears in the equation has the same meaning explained above.

In equation VI, [$S_i$] is the datum which is to be determined at the end of the analysis, and therefore, is not a parameter which the operator can modify at will. The terms Δ, $K_{R-Si}$, ξ and $\gamma^t$ express intrinsic chemical reactivity features of the species present in the analyzed system, and thus are out of operator's control as well. Alternately, the operator of the analysis can modify at pleasure (within certain limits) the terms $C_{Si}^+$ and t, and therefore, these represent "control parameters" of the method of the invention.

The residence time t of the species $S_i^+$ in the reaction zone RZ can be modified through several practical methods. A first way is to change, in the two tests, the value of the electrical field in the reaction zone RZ. In turn this can be achieved by varying in the two tests the electrical field in the whole instrument or selectively only in the reaction zone RZ. This second possibility can be realized by using the IMS instrument that is the object of co-pending Italian patent application No. MI2002A001616. As described in the copending Italian application, the instrument allows to control the electrical field applied in the chamber of the instrument, and in particular to obtain fields with a non-uniform profile along the x axis of said chamber. The preferred kind of non-uniform electrical field is that made up of the sum of two different electrical fields in the zones RZ and DZ. These two electrical field will be referred to as $E_{RZ}$ and $E_{DZ}$, respectively, and are preferably both uniform.

Considering the expression VI above, when the electric field $E_{RZ}$ varies, the value of terms t, $\Delta$ and $\xi$ changes, while the terms $[S_i]$(i=1, ..., n), $[U_j]$(j=1, ..., m), $\gamma$ and the kinetic constants $K_{R-Si}$, $K_{Si-Sj}$ and $K_{Si-Uj}$ do not change. Therefore, by carrying out two tests with two different values of electric field $E_{RZ}$, two values, $C_{1Si}^+$ and $C_{2Si}^+$, are obtained for the charge transported onto the detector by the species $S_i^+$. By using the expression VI, the two charge values can be expressed as:

$$C_{1Si}^+ = [S_i] \times t_1 \times \Delta_1 \times K_{R-Si}/\xi_1 \times \gamma^{t1} \quad \text{(VII)}$$

and $$C_{2Si}^+ = [S_i] \times t_2 \times \Delta_2 \times K_{R-Si}/\xi_2 \times \gamma^{t2} \quad \text{(VIII)}$$

wherein the subscripts 1 and 2 added with respect to the equation VI represent the two analyses carried out with a different field value. By dividing the expression VII by VIII, the invariant terms are canceled, thereby obtaining:

$$C_{1Si}^+/C_{2Si}^+ = (t_1 \times \Delta_1 \times \xi_2)/(t_2 \times \Delta_2 \times \xi_1) \times \gamma^{(t1-t2)} \quad \text{(VIII)}$$

The values of $t_1$, $t_2$, $\Delta_1$, $\Delta_2$, $\xi_1$, e$\xi_2$ and of the ratio $C_{1Si}^+/C_{2Si}^+$ can be obtained from the two spectra. With the two spectra and using equation IX, the value of $\gamma$ is obtained, which can be employed in equation VI for deducing $[S_i]$ without needing to know the reaction constants $K_{Si-Sj}$ and $K_{Si-Uj}$.

The very same effect (i.e., the modification of the residence time of ions $S_i^+$ in the RZ) can be obtained by also modifying the ratio between the flow speeds of the sample gas $F_C$ and of the drift gas $F_D$ or by modifying the length of the reaction zone. The modification of the ratio $F_C/F_D$ can be easily obtained by controlling the flow in the gas lines feeding the sample gas and the drift gas. This can simply be done with needle valves, mass-flow meters, or similar devices known to those skilled in the art. By using this method, only one or both flow speeds can be changed in the two tests. The modification of the length of RZ can be obtained, for instance, by arranging two or more grids in the chamber of the spectrometer, at different points along the instrument axis, and by selectively activating only one of the two grids, i.e., by alternatively "opening" only one of the two grids in the different tests. An IMS instrument provided with two grids is known for example by U.S. Pat. No. 5,200,614 (Jenkins), the contents of which are incorporated by reference herein. But, in the Jenkins patent, the presence of the two grids is used in a different way for a different reason, i.e., for creating a zone in the instrument with an essentially null electric field. As the effect is the same as that obtained by varying $E_{RZ}$, the analysis method is the same too, namely, expressions VII through IX are employed to obtain the value of $\gamma$ that's then employed in expression VI to evaluate the concentration of the species $S_i$.

A second embodiment of the differential method of the invention consists in carrying out two different tests at different values of electric field applied in the drift zone, $E_{DZ}$, and comparing the results thus obtained. The variation in the time of the electric field $E_{DZ}$ allows to solve the non-ideality due to the secondary reactions which take place in the drift zone among the ions $S_i^+$ and the species $B_j$ released by the inner parts of the instrument. The inventors have found that the charge transferred to detector D by the ions $S_i^+$ (indicated in the following as $C_{A,Si}^+$) is linked to the charge quantity actually connected to the ion $S_i^+$ (indicated with $C_{Si}^+$) which comes into the drift zone DZ at the opening of grid G through the relation:

$$C_{A,Si}^+ = C_{Si}^+ \times \lambda^t \quad \text{(X)}$$

where $\lambda$ is a function which considers the charge transfer constants, $K_{Si-Bj}$, between the ions $S_i^+$ and the different additional species $B_i$(i=1, ..., r), released by the material constituting the inner parts of the instrument, and the concentrations $[B_i]$(i=1, ..., r) of these species. By carrying out two tests at different time slots, with a different electric field $E_{DZ}$ in the two tests, the following two relations can be written:

$$C_{1A,Si}^+ = C_{Si}^+ \times \lambda^{t1} \quad \text{(XI)}$$

and $$C_{2A,Si}^+ = C_{Si}^+ \times \lambda^{t2} \quad \text{(XII)}$$

The meaning of the symbols in these relations is analogous to that of the symbols in the equations VII and VIII.

By dividing the equation XI by XII the following equation results:

$$C_{1A,Si}^+/C_{2A,Si}^+ = \lambda^{(t1-t2)} \quad \text{(XIII)}$$

from which $\lambda$ is obtained by measuring the times $t_1$ and $t_2$ in the spectra and obtaining $C_{1A,Si}^+$ and $C_{2A,Si}^+$ from the areas of the peaks relevant to the species $S_i^+$. Once $\lambda$ is known, and by measuring $C_{A,Si}^+$, it is possible to deduce the exact value of $C_{Si}^+$ from the relation X, and therefore, the value of the concentration of the species $S_i$ in the sample gas from the relation VI.

In a third embodiment, the method of the invention consists in carrying out two IMS tests in such experimental conditions as to modify the value of $C_{Si}^+$. In this case, a pair of tests for each species $S_i$ is needed for carrying out a complete analysis of the sample gas. However, the first test can be common to all the pairs of tests. The value of $C_{Si}^+$ can be modified by adding a known concentration of the species $S_i$ to the sample gas. In these conditions, the charge quantity transported to detector D by the i-th species can be described for the two tests by these equations, respectively:

$$C_{1Si}^+ = [S_i] \times t \times \Delta_1 \times K_{R-Si}/\xi_1 \times \gamma^t \quad \text{(XIV)}$$

and $$C_{2Si}^+ = ([S_i]+x) \times t \times \Delta_2 \times K_{R-Si}/\xi_2 \times \gamma^t \quad \text{(XV)}$$

wherein x represents the known concentration of species $S_i$ added in the second test.

In this case, the residence time of the i-th species in the reaction zone remains unchanged, so that in the equations XIV and XV there are no subscripts 1 and 2 for this parameter. The following equation is obtained by dividing equation XIV by equation XV.

$$C_{1Si}^+/C_{2Si}^+ = [S_i]/([S_i]+x) \times (\Delta_1 \times \xi_2)/(\Delta_2 \times \xi_1) \quad (XVI)$$

Also in this case, the values of $C_{1Si}^+$, $C_{2Si}^+$, $\Delta_1$, $\Delta_2$, $\xi_1$ and $\xi_2$ are obtained from the spectra relating to the two tests. Since the term x is known, the only remaining unknown quantity remains concentration $[S_i]$, which can be therefore easily obtained from the previous expression.

The methods of the invention thus allow to overcome the problems of interpretation of IMS spectra of the prior art, avoiding the need to know all the reactions which take place in the instrument chamber and all the relevant kinetic constants and the need to solve a matrix comprising a number of equations equal to the number of primary reactions of type I and secondary reactions of type III, IV or V. Gathering these data, which could be done through complex calibrating procedures, would lead to an extremely burdensome method. Furthermore, also performing a calibration, it would be impossible to consider the reactions of type III, i.e., reactions which take place in the real analysis conditions with unexpected or unknown species. In particular, the first and third described embodiments permit solving the non-ideality problems of the technique due to the presence of secondary reactions of type III, IV and V, while the second described embodiment allows to solve the non-ideality problems due to the presence of species of type $B_j$ in the instrument chamber.

In any embodiments of the method, the spectrum representing the result of the analysis is preferably processed in an automatic way by a suitable known programmable control unit with a microprocessor, for example, a computer provided with suitable interfaces; the values $C_{1Si}^+$, $C_{2Si}^+$, $C_{1A,Si}^+$, $C_{2A,Si}^+$, $t_1$, $t_2$, $\Delta_1$, $\Delta_2$, $\xi_1$ and $\xi_2$, which an operator can employ for obtaining the concentrations of the species $S_i$ (i=1, ..., n) as above described, are obtained as primary data as a result of this automatic analysis. As a preferred alternative, the same unit that analyzes the spectrum, thereby generating the primary data, uses these same data for processing the equations VI to XVI and directly supplies the values of the concentrations of the species $S_i$.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for carrying out analyses of a gas comprising one or more species $S_i$(i=1, ..., n) by using ion mobility spectrometry, the method comprising:
   carrying out a first test with a first set of values of experimental parameters;
   carrying out a second test with a second set of values of the experimental parameters, changing only one parameter chosen among the concentration $[S_i]$ of the species giving rise to ions $S_i^+$(i=1, ..., n), a residence time of the ions in the reaction zone and the residence time of the ions in the drift zone of an ion mobility spectrometer;
   employing the data obtained in the two tests in a relation expressing a charge transferred by the i-th ion to the detector of the spectrometer $C_{Si}^+$ as a function of test parameters, thereby obtaining two equations;
   dividing the two equations by one another, to elimination from the calculation invariant parameters and to obtain as a result of the division at least one parameter that can then be reintroduced in each of the two equations above, and
   outputting the concentration $[S_i]$ of at least one of the species $S_i$(i=1, ..., n).

2. The method according to claim 1, wherein the relation is:

$$C_{Si}^+ = [S_i] \times t \times \Delta \times K_{R-Si}/\xi \times \gamma^t, \text{ and}$$

wherein the parameter changed in the two tests is the residence time t of the ions $S_i^+$(i=1, ..., n) in the reaction zone of the ion mobility spectrometer, the method further comprising:
   carrying out the first test, thereby deducing from the obtained spectrum the values of the terms $C_{1Si}^+$, $t_1$, $\Delta_1$, and $\xi_1$ in the conditions of the first test;
   carrying out the second test, thereby deducing from the obtained spectrum the values of the terms $C_{2Si}^+$, $t_2$, $\Delta_2$, and $\xi_2$ in the conditions of the second test;
   employing the values for obtaining the following two equations:

$$C_{1Si}^+ = [S_i] \times t_1 \times \Delta_1 \times K_{R-Si}/\xi_1 \times \gamma^{t_1} \text{ and } C_{2Si}^+ = [S_i] \times t_2 \times \Delta_2 \times K_{R-Si}/\xi_2 \times \gamma^{t_2};$$

dividing the first of the equations by the second one, thereby obtaining the equation:

$$C_{1Si}^+/C_{2Si}^+ = (t_1 \times \Delta_1 \times \xi_2)/(t_2 \times \Delta_2 \times \xi_1) \times \gamma^{(t_1-t_2)};$$

obtaining the value of $\gamma$ from the latter equation; and
   employing the so obtained value of $\gamma$ in the expression:

$$C_{1Si}^+ = [S_i] \times t_1 \times \Delta_1 \times K_{R-Si}/\xi_1 \times \gamma^{t_1}$$

to obtain the value of $[S_i]$ for at least one of the species $S_i$(i=1, ..., n).

3. The method according to claim 2, wherein t is changed by varying the electrical field in the reaction zone of the instrument, $E_{RZ}$.

4. The method according to claim 2, wherein t is changed by varying the ratio between the flow speed of the sample gas $F_C$ and the flow speed of the counter-flowing gas $F_D$.

5. The method according to claim 2, wherein t is changed by varying the length of the reaction zone by providing an IMS instrument with two grids arranged at different positions along the axis of the ion mobility spectrometer and activating selectively one of the two grids in each of the two tests.

6. The method according to claim 1, wherein the relation is:

$$C_{Si}^+ = [S_i] \times t \times \Delta \times K_{R-Si}/\xi \times \gamma^t, \text{ and}$$

wherein the parameter changed in said two tests is the concentration $[S_i]$ of at least one of the ions $S_i^+$(i=1, ..., n), the change being obtained by adding a known concentration, x, of the species $S_i$ to the sample gas, the method further comprising:
   carrying out the first test, thereby deducing from the obtained spectrum the values of the terms $C_{1Si}^+$, $\Delta_1$, and $\xi_1$ in the conditions of the first test;
   carrying out the second test, thereby deducing from the obtained spectrum the values of the terms $C_{2Si}^+$, $\Delta_2$, and $\xi_2$ in the conditions of the second test;
   employing the values for obtaining the following two equations:

$$C_{1Si}^+ = [S_i] \times t \times \Delta_1 \times K_{R-Si}/\xi_1 \times \gamma^t \text{ and } C_{2Si}^+ = ([S_i]+x) \times t \times \Delta_2 \times K_{R-Si}/\xi_2 \times \gamma^t;$$

dividing the first of the equations by the second one, thereby obtaining equation:

$$C_{1Si}^+/C_{2Si}^+ = [S_i]/([S_i]+x) \times (\Delta_1 \times \xi_2)/(\Delta_2 \times \xi_1); \text{and}$$

obtaining from the latter equation the value of $[S_i]$ for at least one of the species $S_i$ (i=1, ... n).

7. The method according to claim 1, wherein the relation is:

$$C_{A,Si}^+ = C_{Si}^+ \times \lambda^t, \text{ and}$$

wherein the parameter changed in said two tests is the residence time of ions in the drift zone of the ion mobility spectrometer, the change being obtained by varying the electrical field in the drift zone of the instrument, $E_{DZ}$, the method further comprising:

carrying out the first test, deducing from the obtained spectrum the value of the terms $C_{1A,Si}^+$ and $t_1$ in the conditions of said first test;

carrying out the second test, deducing from the obtained spectrum the value of the terms $C_{2A,Si}^+$ and $t_2$ in the conditions of the second test;

employing the values for obtaining the following two equations:

$$C_{1A,Si}^+ = C_{Si}^+ \times \lambda^{t1} \text{ and } C_{2A,Si}^+ = C_{Si}^+ \times \lambda^{t2}$$

dividing the first of the equations by the second one, thereby obtaining equation:

$$C_{1A,Si}^+/C_{2A,Si}^+ = \lambda^{(t1-t2)}$$

obtaining the value of $\lambda$ from the latter equation; employing the so obtained value of $\lambda$ in the expression:

$$C_{1A,Si}^+ = C_{Si}^+ \times \lambda^{t1}$$

for obtaining the value of $C_{Si}^+$; and
introducing the so obtained value of $C_{Si}^+$ in the equation:

$$C_{Si}^+ = [S_i] \times t \times \Delta \times K_{R-Si}/\xi \times \gamma^t$$

for obtaining the value of $[S_i]$ for at least one of the species $S_i$ (i=1, ..., n).

8. The method according to claim 2, wherein the values of the terms $C_{1Si}^+$, $C_{2Si}^+$, $C_{1A,Si}^+$, $C_{2A,Si}^+$, $t_1$, $t_2$, $\Delta_1$, $\Delta_2$, $\xi_1$ and $\xi_2$ are obtained from the spectra resulting from the tests in an automatic way by a programmable control unit with a microprocessor.

9. The method according to claim 8, wherein the unit uses the values for directly supplying the values of the concentrations of the species $S_i$.

10. The method according to claim 8, wherein the unit is a computer provided with interfaces for the connection with the ion mobility spectrometer.

* * * * *